(12) United States Patent
Lehmann et al.

(10) Patent No.: US 8,044,345 B2
(45) Date of Patent: Oct. 25, 2011

(54) METHOD FOR DETERMINING THE CONCENTRATION OF A MOLECULE

(75) Inventors: Wolf Dieter Lehmann, Heidelberg (DE); Dominic Winter, Nackenheim (DE)

(73) Assignee: Deutsches Krebsforschungszentrum, Heidelberg (DE)

( * ) Notice: Subject to any disclaimer, the term of this patent is extended or adjusted under 35 U.S.C. 154(b) by 42 days.

(21) Appl. No.: 12/669,406

(22) PCT Filed: Jul. 14, 2008

(86) PCT No.: PCT/EP2008/059163
§ 371 (c)(1),
(2), (4) Date: Mar. 16, 2010

(87) PCT Pub. No.: WO2009/010489
PCT Pub. Date: Jan. 22, 2009

(65) Prior Publication Data
US 2010/0276585 A1    Nov. 4, 2010

(30) Foreign Application Priority Data

Jul. 19, 2007 (EP) .................................. 07112749

(51) Int. Cl.
*G01N 33/68* (2006.01)
(52) U.S. Cl. ............. 250/282; 435/7.5; 514/44; 530/300
(58) Field of Classification Search .............. 250/282, 250/281; 435/7.5; 514/44; 530/300, 350, 530/403
See application file for complete search history.

(56) References Cited

U.S. PATENT DOCUMENTS
7,473,535 B2 * 1/2009 Aebersold et al. ............. 435/7.5

FOREIGN PATENT DOCUMENTS
WO    WO-01/61028 A2    8/2001
(Continued)

OTHER PUBLICATIONS

Gerber, S. et al. "Absolute quantification of proteins and phosphoproteins from cell lysates by tandem MS", PNAS, Jun. 10, 2003, pp. 6940-6945, vol. 100, No. 12.

(Continued)

*Primary Examiner* — Kiet Nguyen
(74) *Attorney, Agent, or Firm* — Birch, Stewart, Kolasch & Birch, LLP

(57) ABSTRACT

The present invention relates to a method for determining the concentration of a first molecule having a chemical structure, which contains a first peptide sequence comprising:
(a) obtaining a sample containing the first molecule, (b) providing a reference sample which contains a second molecule having a certain concentration and chemical structure, which contains a second peptide sequence, wherein the chemical structure of the second molecule only differs from the structure of the first molecule in one or more permutations in the first peptide sequence, (c) combining the reference sample and the sample containing the first molecule, (d) identifying at least one fragment peak in a mass spectrum (MS) of the first molecule and the second molecule, wherein the mass difference of the fragment peaks is only caused by the permutation of the at least two different amino acids, and (e) determining the concentration of the first molecule relative to the certain concentration of the second molecule by comparing of the identified peaks.

13 Claims, 11 Drawing Sheets

FOREIGN PATENT DOCUMENTS

Figure 1:
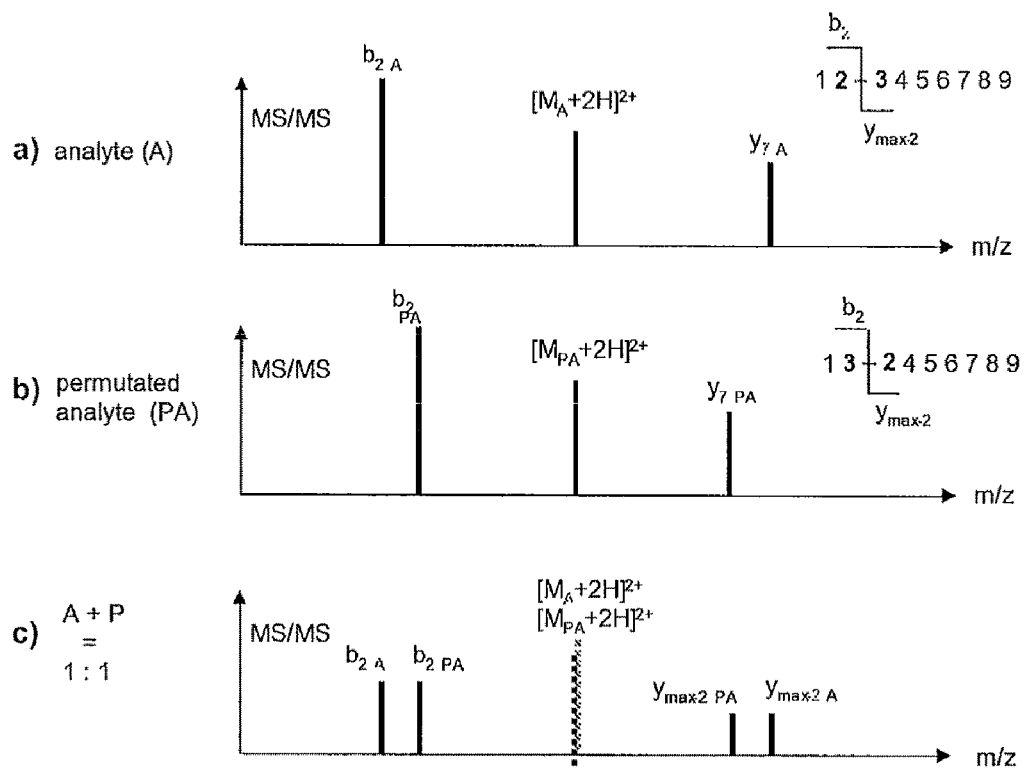

| WO | WO-02/084250 A2 | 10/2002 |
| WO | WO-03/102220 A2 | 12/2003 |
| WO | WO-2006/082389 A1 | 8/2006 |
| WO | WO-2007/031080 A1 | 3/2007 |

OTHER PUBLICATIONS

Oda, Y. et al. "Accurate quantitation of protein expression and site-specific phosphorylation", PNAS, vol. 96, pp. 6591-6596, Jun. 1999.

Bucknall, M. et al "Practical Quantitative Biomedical Applications of MALDI-TOF Mass Spectrometry", J. Am. Soc. Mass Spectrom 2002, vol. 13, pp. 1015-1027.

Van Der Rest, G. et al. "Gas-Phase Cleavage of PTC-Derivatized Electrosprayed Tryptic Peptides in an FT-ICR Trapped-Ion Cell: Mass-Based Protein Identification without Liquid Chromatographic Separation", J. Am. Soc. Mass Spectrom 2001, vol. 12, pp. 288-295.

Written Opinion dated Mar. 9, 2008.

* cited by examiner

SEQUENCE LISTING

```
<160> NUMBER OF SEQ ID NOS: 10

<210> SEQ ID NO 1
<211> LENGTH: 8
<212> TYPE: PRT
<213> ORGANISM: Artificial Sequence
<220> FEATURE:
<223> OTHER INFORMATION: Synthetic peptide derived from Galectin-1
      protein

<400> SEQUENCE: 1

Ser Phe Val Leu Asn Leu Gly Lys
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic peptide for proof of principle

<400> SEQUENCE: 2

Ser Phe Leu Val Asn Leu Gly Lys
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic peptide for proof of principle

<400> SEQUENCE: 3

Ser Phe Leu Leu Asn Val Gly Lys
1               5

<210> SEQ ID NO 4
<211> LENGTH: 3
<212> TYPE: PRT
<213> ORGANISM: Artificial Sequence
<220> FEATURE:
<223> OTHER INFORMATION: Synthetic peptide for proof of principle

<400> SEQUENCE: 4
```

```
Leu Asn Val
1

<210> SEQ ID NO 5
<211> LENGTH: 8
<212> TYPE: PRT
<213> ORGANISM: Artificial Sequence
<220> FEATURE:
<223> OTHER INFORMATION: Synthetic peptide for proof of principle

<400> SEQUENCE: 5

Ser Phe Leu Val Asn Leu Gly Lys
1               5

<210> SEQ ID NO 6
<211> LENGTH: 3
<212> TYPE: PRT
<213> ORGANISM: Artificial Sequence
<220> FEATURE:
<223> OTHER INFORMATION: Synthetic peptide for proof or principle

<400> SEQUENCE: 6

Val Asn Leu
1

<210> SEQ ID NO 7
<211> LENGTH: 8
<212> TYPE: PRT
<213> ORGANISM: Artificial Sequence
<220> FEATURE:
<223> OTHER INFORMATION: Synthetic peptide for proof of principle

<400> SEQUENCE: 7

Ser Phe Leu Leu Asn Val Gly Lys
1               5

<210> SEQ ID NO 8
<211> LENGTH: 4
<212> TYPE: PRT
<213> ORGANISM: Artificial Sequence
<220> FEATURE:
<223> OTHER INFORMATION: Synthetic peptide for proof of principle

<400> SEQUENCE: 8

Leu Leu Asn Val
1

<210> SEQ ID NO 9
<211> LENGTH: 8
<212> TYPE: PRT
<213> ORGANISM: Artificial Sequence
<220> FEATURE:
<223> OTHER INFORMATION: Synthetic peptide for proof of principle

<400> SEQUENCE: 9

Ser Phe Val Leu Asn Leu Gly Lys
1               5

<210> SEQ ID NO 10
<211> LENGTH: 4
<212> TYPE: PRT
<213> ORGANISM: Artificial Sequence
<220> FEATURE:
<223> OTHER INFORMATION: Synthetic peptide for proof of principle
```

```
<400> SEQUENCE: 10

Val Leu Asn Leu
1
```

METHOD FOR DETERMINING THE CONCENTRATION OF A MOLECULE

The present invention relates generally to the fields of analytics of proteins and peptides. More particularly, the invention concerns determination of the concentration of a molecule, protein or peptide in a sample by mass spectrometry (MS).

With the completion of the Human Genome Project, the emphasis is shifting to examining the protein complement in the human organism. This has given a rise to the science of proteomics, the study of the whole amount of the proteins produced by a cell type of an organism. At the same time, there has been a revival of interest in proteomics in many prokaryotes and lower eukaryotes as well.

The term proteome refers to all the different proteins expressed by a genome and thus involves the identification of proteins in the body and the detection of their physiological and pathophysiological function. The about 30,000 genes, defined by the Human Genome project translate into 30,000 up to 1 million of proteins, when alternate splicing and post-translational modifications are considered. While a specific genome remains unchanged to a high extent, the proteins in any particular cell change dramatically as genes are turned on and off in response to extracellular stimulation.

As a reflection of the dynamic nature of the proteome, the term "functional proteome" is preferred by some scientists, which describes the whole amount of proteins produced by a single cell in a single time frame. Finally, it is believed, that through proteomics, new disease markers and drug targets can be identified that will help design new products to prevent, diagnose and treat disease.

The true primary themes in proteomics are protein identification and the comparison of the protein expression levels into physiological or pathological states (comparative proteomics). The long-term goal of being able to define the entire proteome of a cell is still unrealized, but the characterization of many thousands of proteins in a single analysis is now attainable.

For proteomics to become a platform technology serving the emergent field of systems-biology, there is a processing need for enhancement of quantification. Most comparative proteomic studies deliver a relative quantification, expressing the changes in concentrations of a protein in the context of a different cellular stage. However, the goal must automatically be to define the cellular concentrations of proteins absolutely, whether as molarities or as numbers of molecules per cell. Absolute quantification, which poses one to the greatest challenges in proteomics, draws on well-established percepts in analytical chemistry and requires either external standards or internal standards. External standardization is typified by immuno detection, whether solution phase or on position-addressable antibody arrays. The second approach, reliant on internal standardization, is based on mass spectrometry (MS), wherein highly selective detection of ions (or ion fragmentations) characteristic of the analytes of interest is combined with the use of internal standards.

In the most MS-analysis, stable isotopic variants of the analysis are used as internal standards. The key-underlying principle is that the termination of relative signal intensities during mass spectrometric analysis can be converted into absolute quantities of analyte by reference to an authentic standard available in known concentrations. The direct application of this approach to intact proteins is impractical and it is common to adopt the principle to quantify indirectly by reference to a proteolytic peptide derived from the protein of interest.

Analysis based on the principles using internal standards synthetisized de novo by chemical methods have been named "AQUA" (Absolute Quantification) (Gerber PNAS 100 (2003), 1940-6945). Wherever, this approach does not lend itself well to absolute quantification of large numbers of proteins, as each peptide would need to be chemical synthesized, labeled isotopically and independently quantified.

The international patent application WO 03/102220 provides methods to determine the absolute quantity of proteins present in a biological sample. The principle of WO 03/102220 is based on the generation of an ordered array of differently isotopically tagged pairs of peptide, wherein each pair represents a unique protein, as specific protein isoform or as specifically modified form of a protein. One element of the peptide pairs is a synthetically generated, external standard, and the other element of the pair is a peptide generated by enzymatic digestion of the proteins in a sample mixture. For performing the method of WO 03/102220, the standard peptides are calibrated so that absolute concentrations are known and added for comparison and quantification. A sample of interest is also labeled with the same isotope tag as used for the standard peptides except differing in the isotopic label. The signal pairs, which correspond to differently labeled samples and standard peptides are finally observed and related to a list of expected methods based on the particular standard peptides included. The disadvantages of this patent application are that standard peptides are isotopically targeted and need to be individually synthesized, purified and quantified. Moreover, both the sample and the standard peptides need to be specifically labeled separately, increasing the potential for variability between experiments.

Other methods for proteome analysis include quantitative mass spectrometry based on multidimensional peptide separation and isotope-coded affinity tagging of proteins. This method allows relative quantitation, that is, that the termination of the abundance ratio of each protein into samples does not allow the termination of the absolute quantity of the proteins in a sample. Also, chip technology using arrays of reagents with known specifity for target proteins, such as antibody arrays or arrays of aptamers, can be used for proteomic analysis. However, the use of such arrays can be limited to the need to selectivity, capture representative proteins or preserve the three-dimensional structure of the proteins depending on the particular use of a chip.

Each quantitation approach has advantages and disadvantages. Quantification of protein expression ratios by metabolic labeling, such as a stable isotope labeling in cell culture (SILAC) (Oda Y., Huang K., Cross F. R., Cowburn D., Chait B. T., Proc. Natl. Acad. Sci. USA, 1999, Vol. 96, 6591-6596) strategy provides the opportunity to redundantly quantify protein, but has the limitation that primary tissue cannot be analyzed.

Thus, there is still an existing need to develop easy and convenient methods for absolute quantification of molecules, proteins or peptides without using isotopically labeled molecules, proteins or peptides.

Accordingly, an aim of the present invention is to provide a method for determining the concentration of a molecule avoiding the draw backs mentioned above.

This is achieved by a method for determining the concentration of a first molecule having a chemical structure, which contains a first peptide sequence comprising:
(a) obtaining a sample containing the first molecule,
(b) providing a reference sample which contains a second molecule having a certain concentration and chemical structure, which contains a second peptide sequence, wherein the chemical structure of the second molecule only differs from the structure of the first molecule in one or more permutations in the first peptide sequence, (c) combining the reference sample and the sample containing the first molecule, (d) identifying at least one fragment peak in a mass spectrum (MS) of the first molecule and the second molecule, wherein the mass difference of the fragment peaks is only caused by the permutation of the at least two different amino acids, and (e) determining the concentration of the first molecule relative to the certain concentration of the second molecule by comparing of the identified peaks.

It was found that the method according to the invention is a surprisingly easy way for the determination of concentrations. Advantageously, the method according to the present invention allows quantification of protein expression ratios in primary tissue as metabolic labeling such as stabile isotope labeling is not necessary.

According to one embodiment of the invention, the second molecule of known amount is added to the reference sample and the absolute concentration of the first molecule in the sample is determined in step e) of the method of the invention.

The term "first molecule" having a chemical structure encompasses proteins, polypeptides, peptides and other molecules which contain a peptide sequence. As used herein, the term "polypeptide" refers to a peptide or a polypeptide of two or more amino acids. A polypeptide can also be modified by naturally occurring modifications, such as post-translational modifications, including phosphorylation, fatty acylation, sulfatation, hydroxylation, acetylation, adding of carbohydrate, addition of prosthetic groups or cofactors, formation of disulfide bonds, proteolysis, assembly into molecular complexes and the like.

As used herein the term "sample" is intended to mean any biological fluid, cell, tissue, organ or portion thereof that includes one or more different molecules, such as nucleic acid, polypeptides, or small molecules. As sample can be a tissue section obtained by a biopsy or cell that are placed in or adapted to tissue culture. A sample can also be a biological fluid, specimen such as blood or plasma, cerebrospinal fluid, urine, saliva, seminal plasma, pancreatic juice, and the like. A sample can additionally be a cell extract from any species, including procaryotic and eucaryotic cells as well as viruses. A tissue or biological fluid specimen can be further fractionated, if desired, to a fraction containing particular cell types.

The methods of the invention are based on the identification and quantification of distinct molecules, particularly peptides which are unique for a polypeptide and come well for the use to identify the presence and quantity of the polypeptide in a sample. Peptides uniquely identifying a protein can be selected experimentally or computationally. Experimentally such peptides are selected from databases that contain all the peptides from a species that to have been previously observed, for example by mass spectrometry experiments. Computationally such peptides are selected by translating the complete genomic sequence or the sequence of all predicted genes and their splice forms into the corresponding amino acid sequences, by applying the rules for cleavage that are predictable with each chemical or enzymatic protein cleavage reagent to these amino acid sequences by computing the sequence, mass and other properties for each of the generated peptides. From this database of predicted peptides, a suitable selection of peptides that are unique for each target protein is then selected and observed.

After selection of the first molecule which contains a peptide sequence, a second molecule having a chemical structure which differs from the first molecule only in at least one, preferably only one, permutation of different amino acids in the peptide sequence is made by synthesis. The permutation can be made for adjacent and non-adjacent amino acids. According to this, a permutation analog to the first peptide is synthesized that is usable as the second molecule according the invention. The permutation analog sequence is derived from the first peptide sequence by the positional exchange of two amino acids, preferably of two related, homologous amino acids. Hence, a typical "second peptide" is realized when two adjacent amino acids are exchanged in their position, as for instance in the "theoretical second" peptide 1-3-2-4-5-6-7-8, in comparison to the "theoretical first peptide" 1-2-3-4-5-6-7-8. Both theoretical peptides are exactly isobaric, but can be discriminated by their specific fragment ion spectrum by the means of MS/MS.

The peptide sequences, once selected, are preferably chemically synthesized by solid-phase stepwise synthesis and, if necessary, quantified. Methods of synthesizing peptides are well known to those skilled in the art. According to an embodiment of the invention, for each peptide or second molecule, a calibrated stock solution is prepared and stored. Quantification of the calibrated stock solution can be carried out by quantitative amino acid composition analysis, can be based on UV absorbance measurement or other spectrometric methods, by weighing the dried peptide or a combination thereof The peptide of the second molecule carries at least one permutation of different amino acids in its sequence. In general, the permutation will not affect the overall fragmentation efficiency, so that the corresponding fragmentations of the permutated and non-permutated peptide will be detected with very similar signal intensity. Preferably, control experiments for samples containing only the first and second peptide, respectively, are performed to prove this situation or to document exceptions from this rule in a quantitative way. If relevant, this control measurement provides a correction factor, which can be used to calculate the relative concentration of the first peptide from the raw data. In other words, the true molar abundance ratio of the two peptides is calculated from the original or the corrected intensity ratio of two peptide-specific fragment ion intensities. Based on the known concentration of the second peptide, the concentration of the first molecule original present in the sample is deduced. Thus, the method of invention can be used to determine the relative concentrations of molecules present in the sample as well as absolute concentrations, if the solution of the second peptide is quantified. Preferably a control measurement between the first and the second molecule is made to reveal exceptions to this rule. The control measurement then provides a correction factor, which can be used to calculate the relative concentration of the first molecule from the raw data. In other words, from the combined signal intensities for a molecule pair, the ratio of abundance is calculated. Based on the known concentration of the second molecule bearing peptide, the concentration of the first molecule initially present in the sample is deduced. Thus, the method of the invention can be used to determine relative concentrations of molecules present in the sample as well as absolute concentrations by comparison to the quantified second molecule.

According to a preferred embodiment of the invention, a reference sample is used in step (b) which contains a second molecule having a certain concentration and chemical structure, which contains a second peptide sequence, wherein the chemical structure of the second molecule only differs from the structure of the first molecule in at least one or more conservative permutations in the first peptide sequence.

As used herein, the expression "at least one conservative permutation" means, that amino acids of the same class are permutated, such as non-polar like glycine, alanine, valine, leucine, isoleucine, proline, methionine, phenylalanine, and tryptophan, or polar amino acids like serine, threonine, aspargine, glutamine, cysteine, tyrosine, or acidic amino acids like aspartic acid, and glutamic acid, or basic amino acids like lysine, arginine, or histidine. According to the invention, the second molecule contains one to five permutations, more preferable one to two permutations, most preferable one permutation.

A method is preferred, wherein at least one of the pairs of amino acids selected from the group consisting of serine and threonine; asparagine and glutamine; aspartic acid and glutaric acid; and lysine and arginine is permutated.

The inventor has found that it is advantageous when the mass spectrometer further to comprises an upstream liquid chromatograph. Suitable chromatographs include, but are not limited to, liquid chromatography (LC), high performance liquid chromatography (HPLC), ultra performance liquid chromatography (UPLC)).

According to the invention, the reference sample containing the second molecule is combined with the sample containing the first molecule, and the samples are separated by liquid chromatography and/or mass spectrometry and thereinafter analyzed in a mass spectrometer, preferred in a tandem mass spectrometer (MS/MS) under identical conditions, since both the first and the second molecule are always fragmented exactly simultaneously under identical instrumental settings. The different fragment peaks of the first and the second molecule caused by the permutation are identified and the relative concentration for the first molecule in the sample is determined by comparison of identified peaks, optionally taking into account the correction factor determined above. Since the concentration or the absolute amount of the second molecule is known, and the ratio between concentrations or amounts of the first and the second molecule can be determined from the mass spectra, the concentration of the first molecule can be calculated. Using this approach, e.g. the levels of proteins and post-translational modifications can be accurately measured.

The method of the invention can be used in a variety of different applications. For example, the methods of the invention can be used for profiling blood serum. The possibility to analyze readily accessible specimens such as blood serum is particular useful for clinical applications. Hence, the methods are also applicable to basic biology and clinical analysis.

The method according the invention can also be applied to the mapping and profiling of post-translational modifications. Thus, the invention provides a method fort he quantitative profiling of post-translational modifications. For profiling of polypeptides having post-translational modifications, a modified peptide having a known post-translational modification is chemically synthesized and used in the methods of the invention as second molecule, as described above.

According to an embodiment of the invention, the permutation in the protein sequence of the second molecule leads to a predetermined breaking point within the peptide sequence of the second peptide. For example, such a breaking point is present in the peptide sequence, when the permutation is conducted in a way that leads to two adjacent proline amino acids.

In a preferred embodiment of the invention, the first peptide sequence has 5 to 100 amino acids, more preferred 5 to 50 amino acids, most preferred 6 to 20 amino acids.

According to a further embodiment of the invention, the first and the second molecules can be synthesized by tagging of a first peptide and a second permutated analogue peptide to a molecule, peptide or pharmaceutically active compound that allows identification and relative quantification of the same unique molecule, peptide or pharmaceutically active compound under different cellular stages. Accordingly, a method is preferred, wherein the first molecule is a pharmaceutically active compound.

Due to the fact, that the two resulting molecules are compositionally identical but distinguished only in their peptide sequence, they often will co-purify. The addition of a known concentration of one of the first tagged molecules allows direct comparison and determination of the concentration of the corresponding second molecule. However, with high or ultra-performance liquid chromatography, they may be completely separated. The permutated peptides may be separated from peptides with "unpermutated" sequence by liquid chromatography (LC). Thus, liquid chromatography (e.g. with UV detection) in combination with mass spectrometry can be used for peptide/protein quantification using peptides as internal standards, in case their elution sequence has been clarified using e.g. pure standards peptides and LC-MS/MS.

Another method is preferred, wherein the first molecule is obtained by linking a peptide having a peptide sequence containing the first peptide sequence to a pharmaceutically active compound. In general, the first molecule can be a polypeptide.

To investigate the relative quantity of the first and the second molecule, two samples containing either the first or the second molecule were prepared gravimetrically at equal concentrations, mixed in the following proportions: 9:1, 8:2, 7:3, 6:4, 5:5, 4:6, 3:7, 2:8, and 1:9, and were analyzed using a tandem MS (MS/MS) spectrometer. In the tandem MS spectrometer a sample is "sorted" and "weighed" in the first mass spectrometer, then broken into the specific fragments and the collision cell and a piece or pieces are weighed in the second mass spectrometer. Collision offset plots were recorded by nano-ESI QTOF tandem mass spectrometry for these mixtures as well over two solutions of the pure first or the second molecule. An offset plot requires the sequential recording of MS/MS spectra for a series of collision offset values over a selected range. From this set of data, the intensity of each fragment ion can be displayed as a function of the collision offset for the first or second molecule. Since the exact concentration of the second molecule is known, the absolute concentration of the first molecule can be determined using the method of the invention.

The methods of the invention are advantageous because they obviate the need for antibodies, aptamers or other reagents that are specific for a particular protein for the analysis of polypeptide expression profiles. However, in the present invention, all that is needed is a synthetic second molecule having a chemical structure which differs from the chemical structure of the first molecule only by at least one conservative permutation in its peptide sequence. Such a molecule can be generated in a few hours, and many peptides can be generated in parallel.

The following figures and the examples are included to further illustrate various aspects of the present invention. It should be appreciated by those of skilled in the art that the techniques disclosed in the examples which follow the presented techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and the scope of the invention.

FIGURES

FIG. 1: FIG. 1 shows a fragment ion spectrum of two peptides which are isobaric, but can be discriminated by their fragment ion spectrum.

Figure 2:
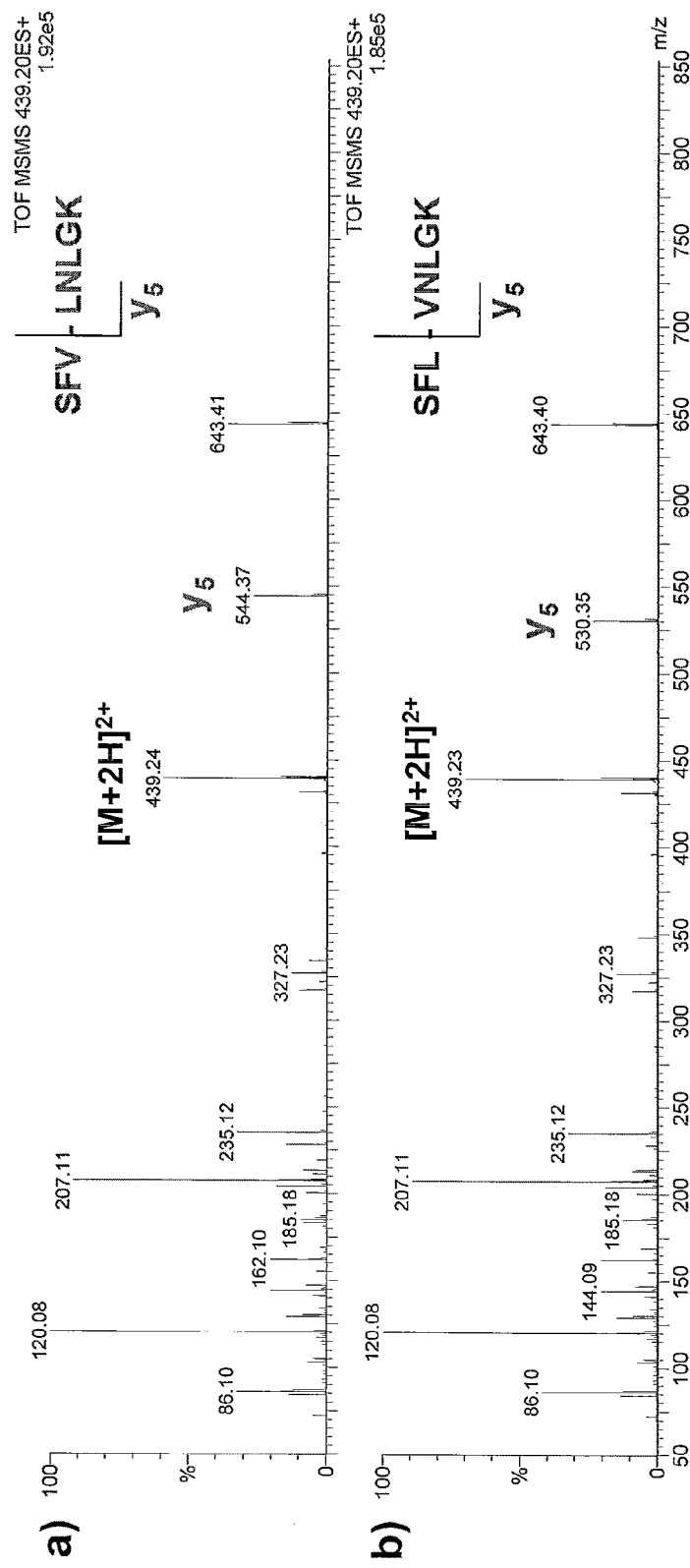

FIG. 2: FIG. 2 shows the fragment ion spectra of the first molecule SFVLNLGK (SEQ ID NO: 1) (a) and the fragment ion spectrum of the corresponding second molecule SFLVNLGK (SEQ ID NO: 2) (b).

Figure 3:
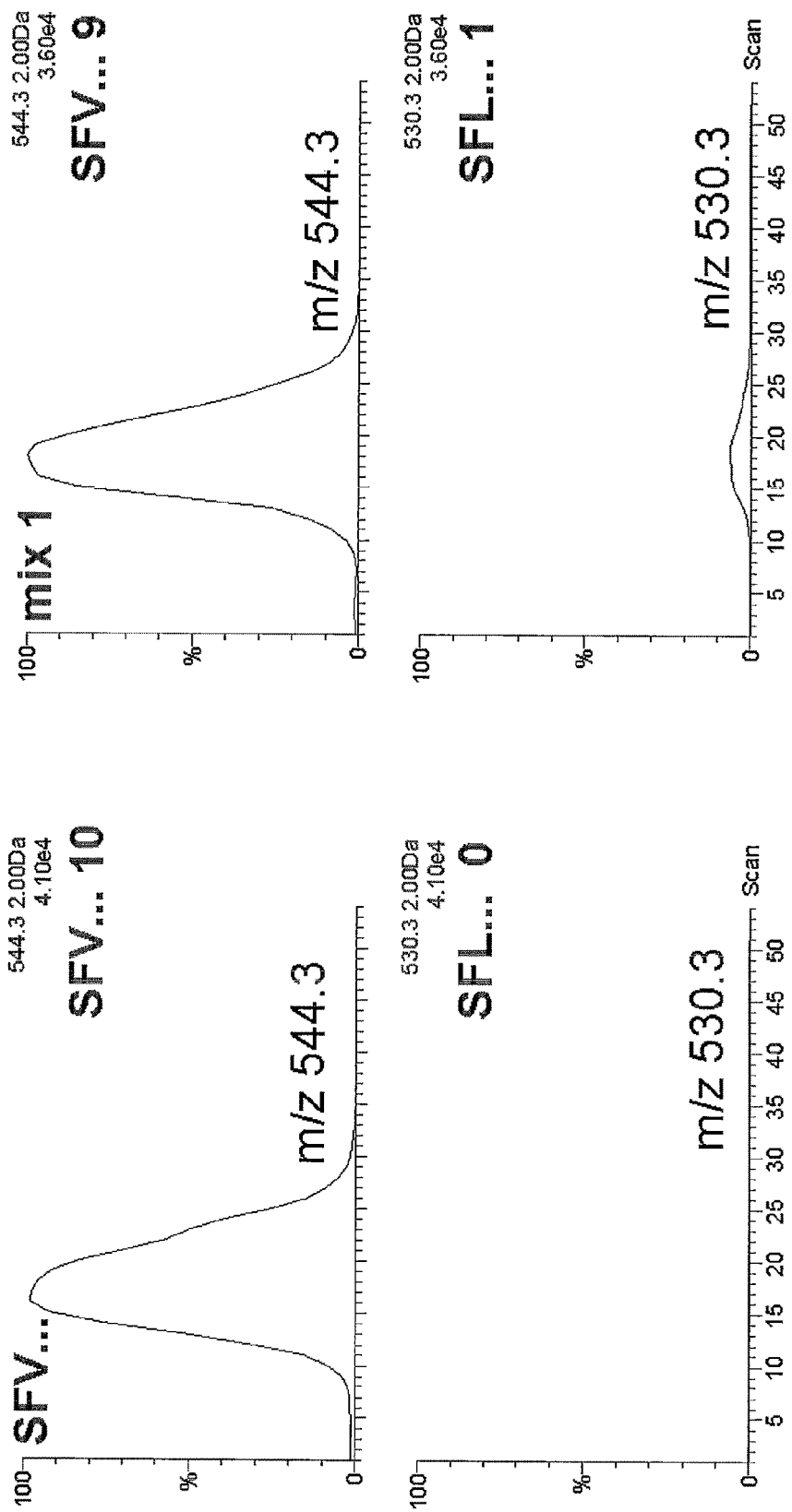
Figure 3:
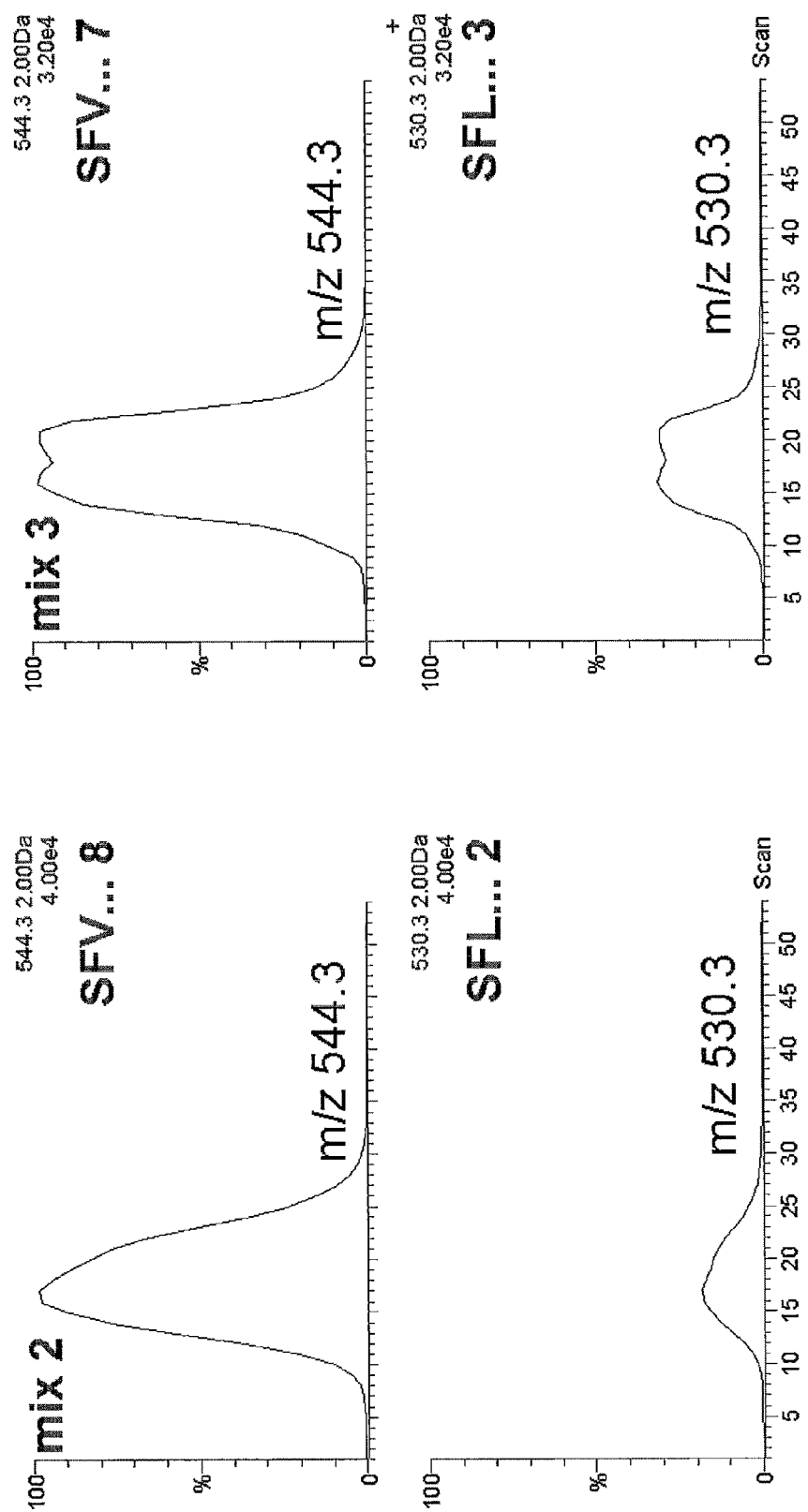
Figure 3:
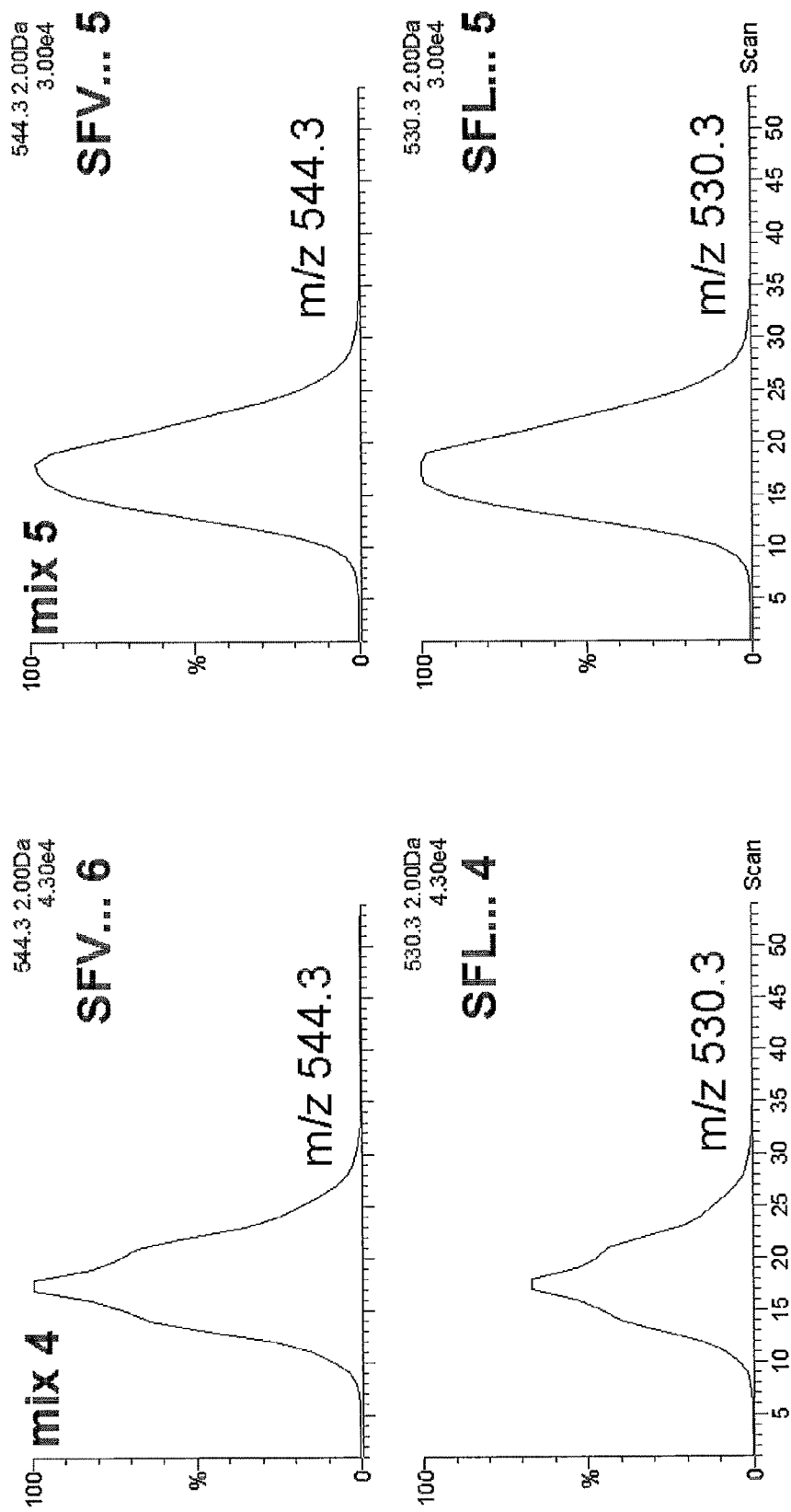
Figure 3:
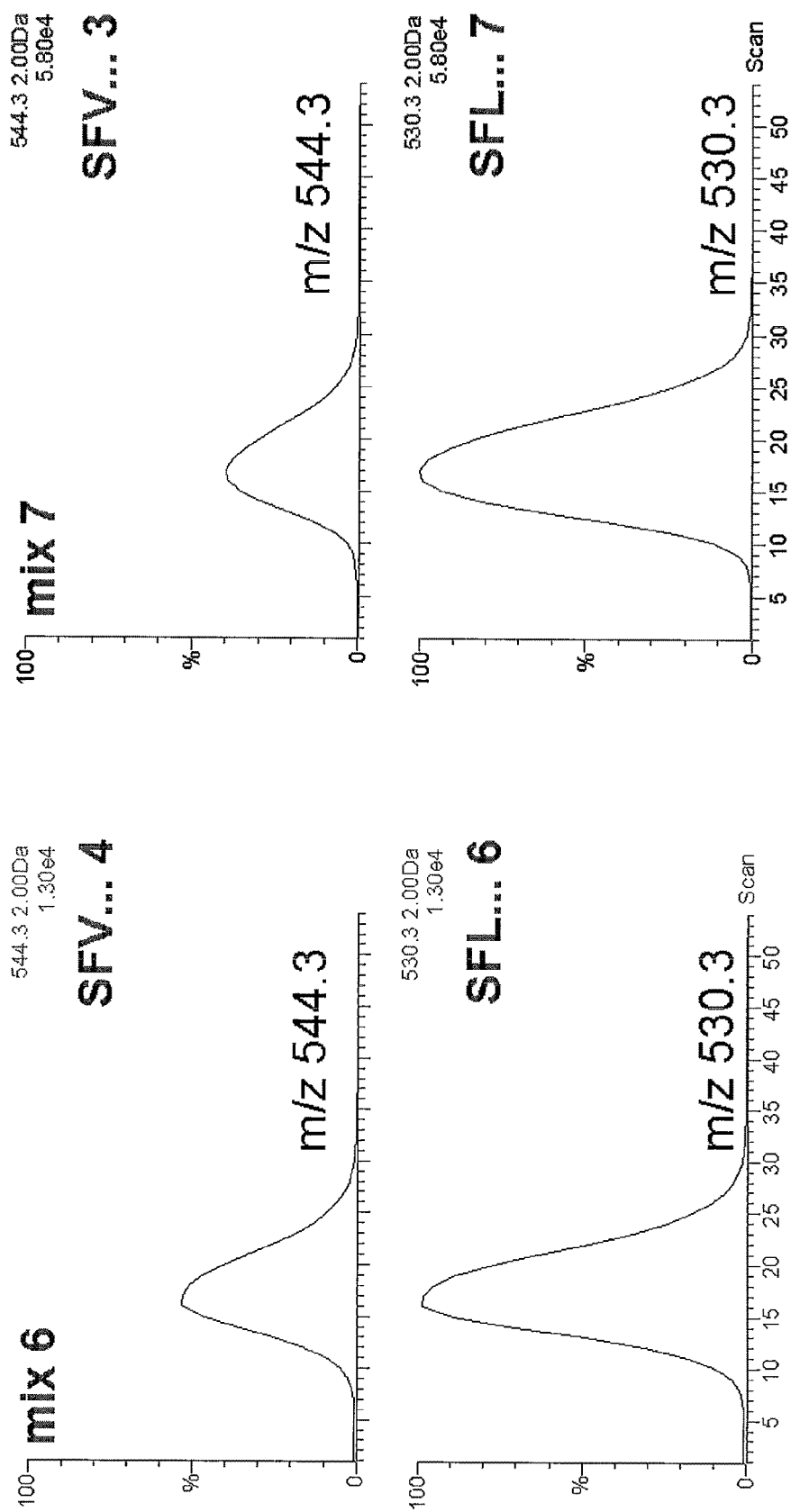
Figure 3:
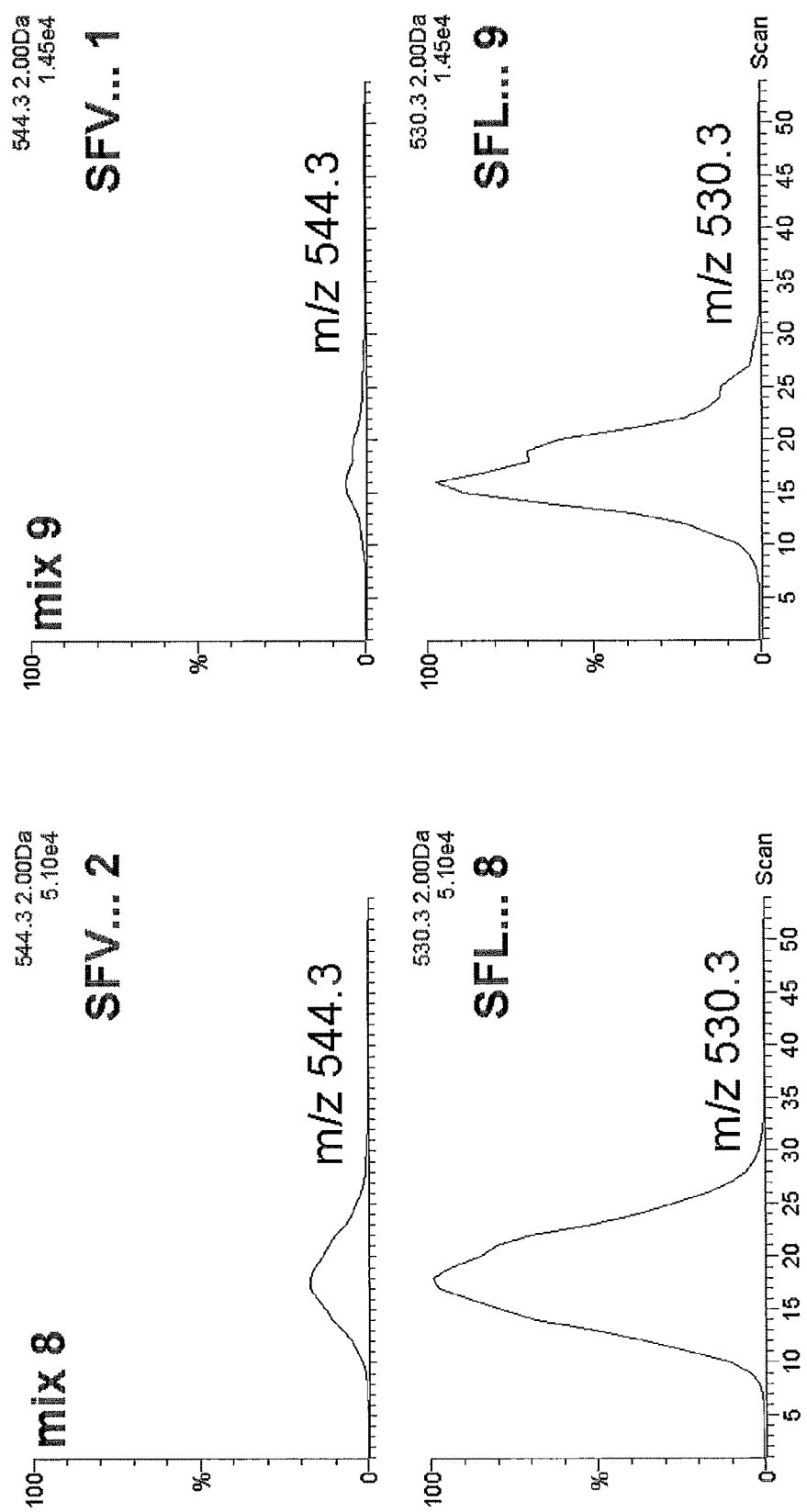
Figure 3:
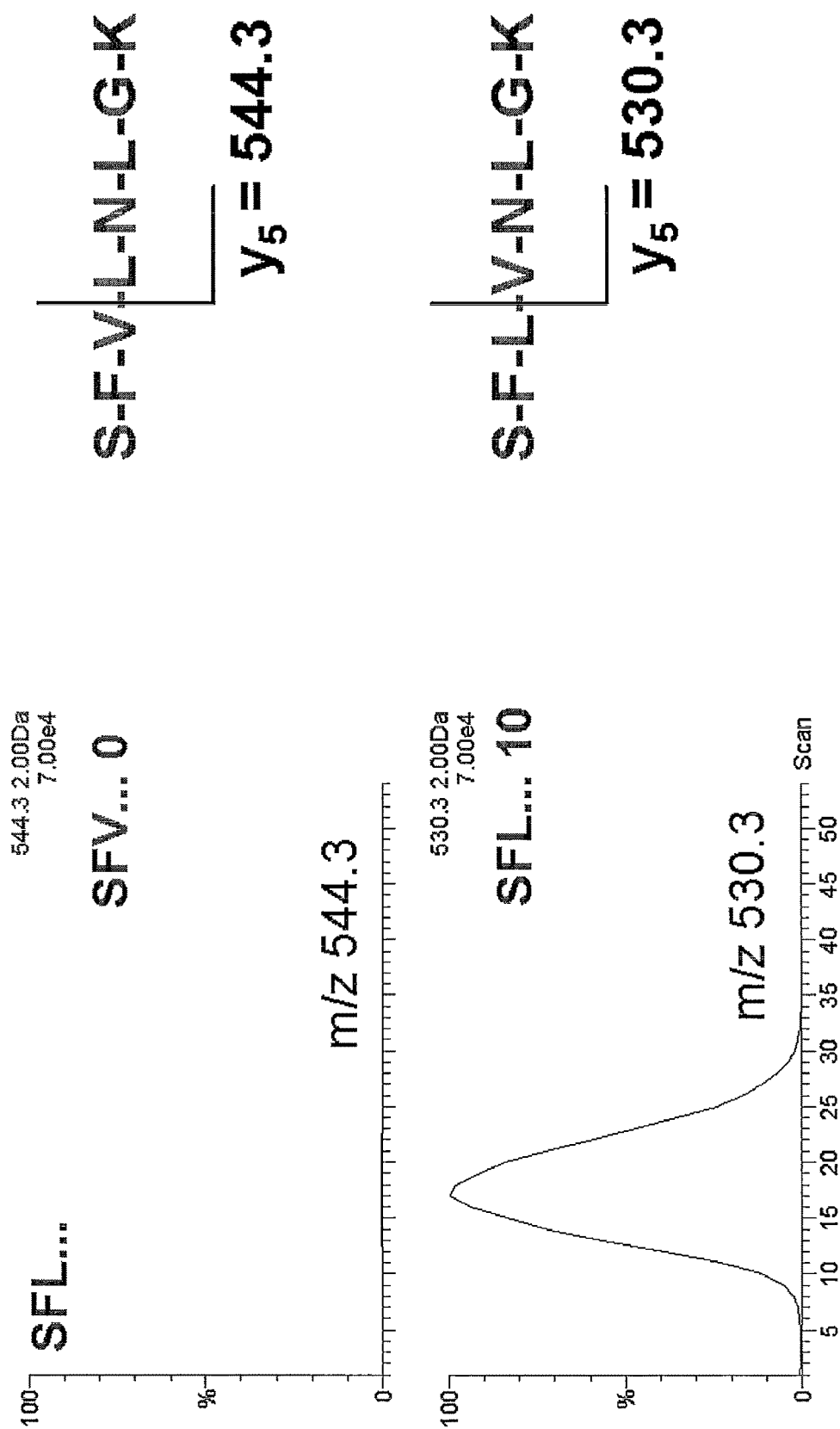

FIG. 3: FIG. 3 shows collision offset plot data for the $y_5$-ions of the first and the second molecule as described in FIG. 2. Eleven samples were analyzed, including the two pure molecules (first and last plot, respectively), as well as nine first/second molecule mixtures with the relative compositions 9:1, 8:2, 7:3, 6:4, 5:5, 4:6, 3:7, 2:8, and 1:9, as indicated.

Figure 4:
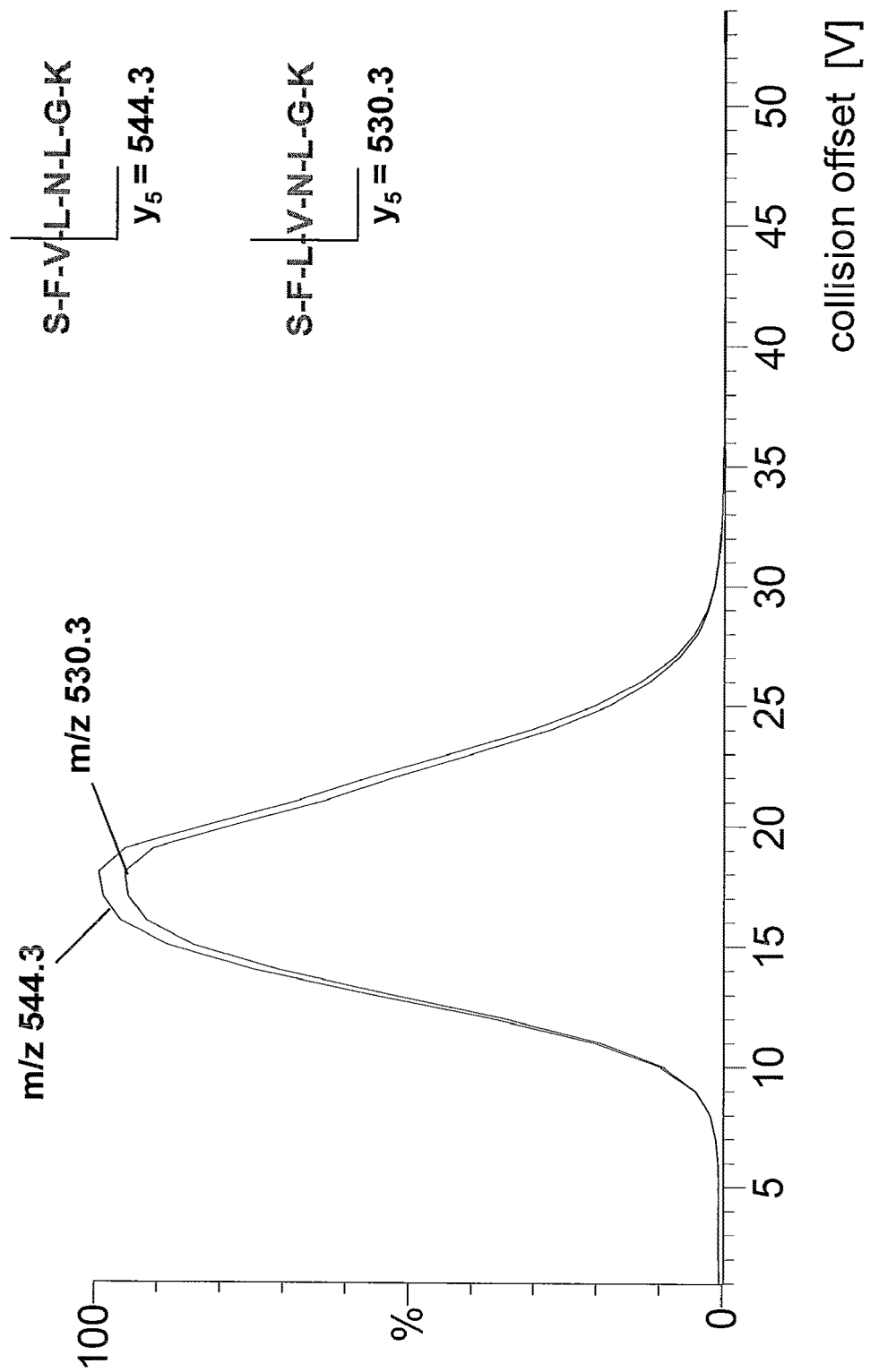

FIG. 4: FIG. 4 shows an overlay plot of the collision offset profiles for the $y_5$-ions of a 1:1 mixture of the first molecule (m/z 544.3) and the second molecule (m/z 530.3) as recorded by ESI-MS/MS.

Figure 5:
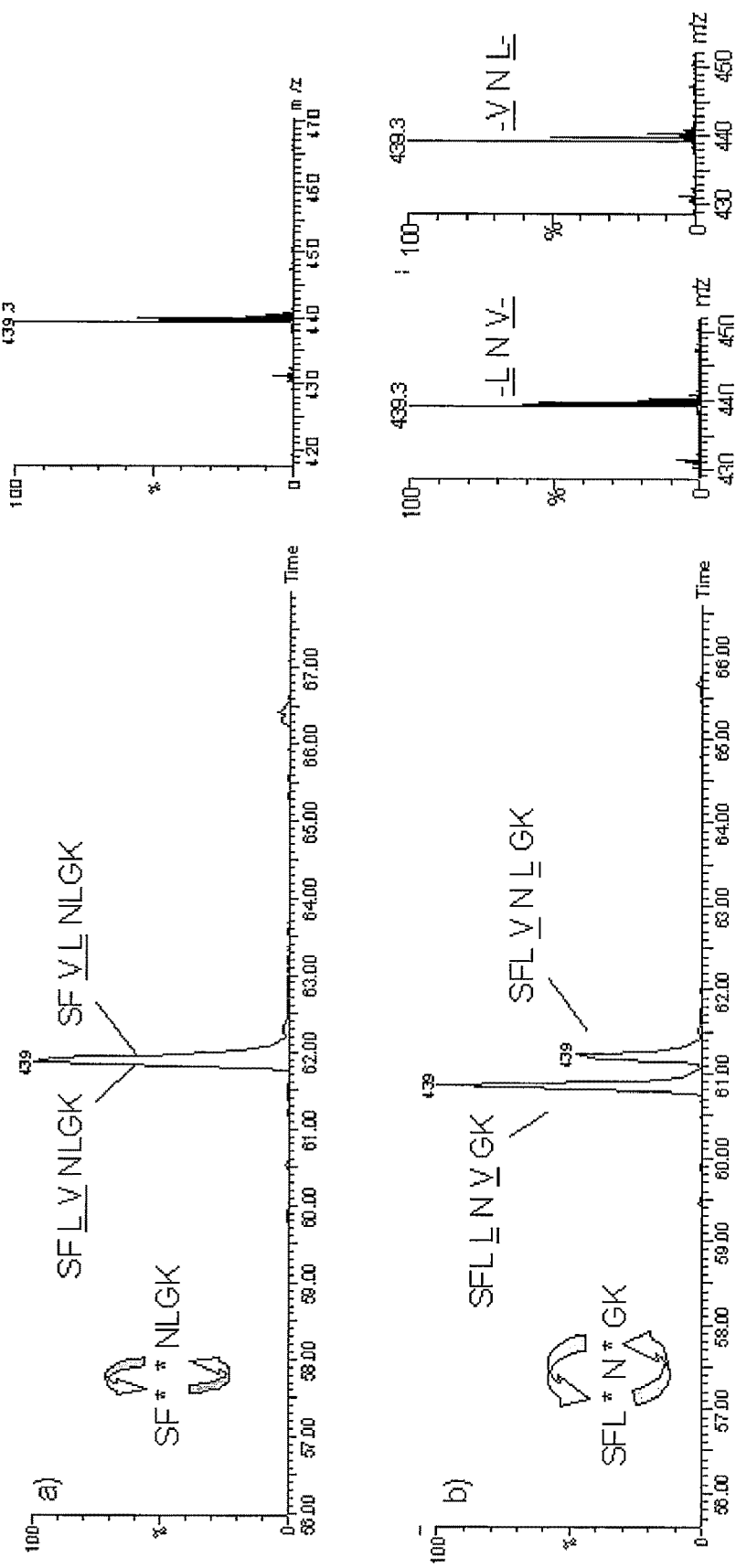
Figure 5:
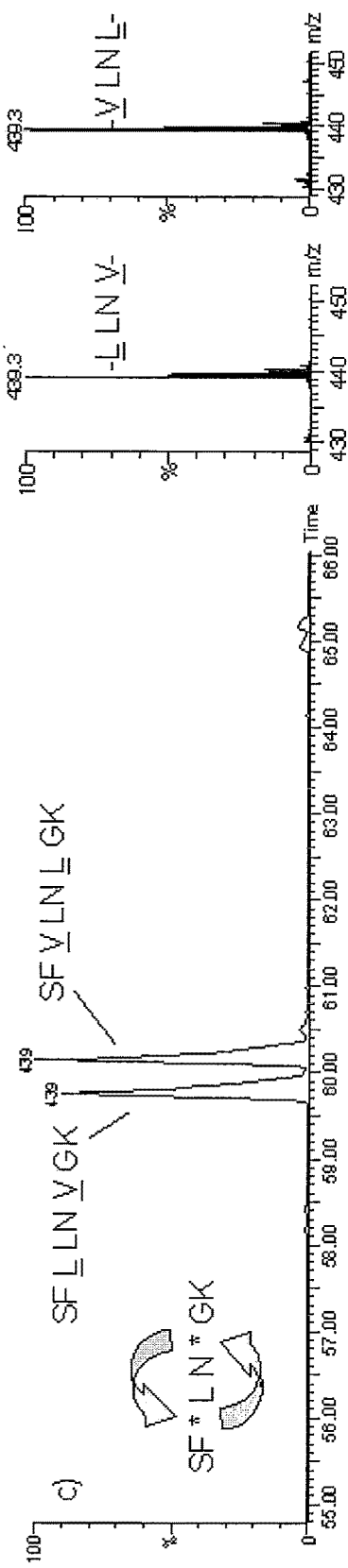

FIG. 5: FIG. 5 shows UPLC (ultra performance liquid chromatography) MS analysis of three binary mixtures, each comprising a first and a second molecule of the invention, (a) SFLVNLGK (SEQ ID NO: 2) and SFVLNLGK (SEQ ID NO: 1); exchange of two adjacent residues was performed; (b) SFLLNVGK (SEQ ID NO: 3) and SFLVNLGK (SEQ ID NO: 5); exchange of two amino acids separated by one residue was performed (SEQ ID NOS: 4 and 6); (c) SFLLNVGK (SEQ ID NO: 7) and SFVLNLGK (SEQ ID NO: 9); exchange of two amino acids separated by two residues was performed (SEQ ID NOS: 8 and 10). The mass spectra show the [M+2]$^{2+}$ ions of the isobaric peptides as acquired over the corresponding LC-peaks. The peptide pair in (a) was not separated, whereas the peptide pairs analyzed in (b) and (c) could be baseline-separated.

In FIG. 1, exemplary first and second molecules are shown. In this example, the typical second molecule is realized when two adjacent amino acids are exchanged in their position, as for instance in the theoretical second molecule 1-3-2-4-5-6-7-8 in comparison to the theoretical first molecule 1-2-3-4-5-6-7-8, whereby the two molecules are peptides respectively. Both molecules are exactly isobaric, but can be discriminated by their fragment ion spectrum, as shown in FIG. 1. For simplicity only the pair of $b_2/y_{max-2}$ ions is shown; a) MS/MS spectrum of the first peptide (A) sequence 1 23456789; b) MS/MS spectrum of the second peptide 1 32456789, in which the amino acids in position 2 and 3, which must have different masses, have been exchanged in their sequence position; c) MS/MS spectrum of a 1:1 mixture of the first and the second peptide. The relative concentration or quantity of the peptides of the 1:1 mixture can be read from the corresponding signal intensities for the $b_2$ or $y_{max2}$ ion pairs. As outlined in FIG. 1, the relative concentration of a first molecule A and second molecule B is performed by tandem mass spectrometry. In general, a permutation of a peptide sequence will not affect the corresponding fragment ion formation efficiency, i.e. that $b_2$ and $y_7$ ions of the isobaric ions are detected with identical signal intensity. The control measurement (see below) will reveal exceptions to this rule, i.e. those cases where a permutation may affect fragment ion intensities.

The control measurement then provides a correction factor, which can be used to calculate the relative analyte concentrations from the raw data.

The control measurement can be conducted in two ways:

Control Method 1:

The first and the second molecule are synthesized and mixed in 1:1 ratio (e.g. from gravimetrically defined solution) and complete collision offset profile MS spectra are recorded. From the fragment ions detected, one or more ion pairs are selected for optimally specific and optimally sensitive quantification.

Control Method 2:

Synthesis of an enzyme-cleavable tandem peptide (see patent application EP 06113151.2), one part representing the first molecule, the other part the second molecule. Upon enzymatic cleavage an exactly 1:1 molar mixture of first and second molecule is obtained. This mixture is analyzed as described for control method 1.

EXAMPLE 2

For the proof of principle of the present invention, a first and a second molecule in form of a first and a second peptide were synthesized. The first peptide SFVLNLGK (SEQ ID NO: 1), representing a natural sequence from the galectin-1 protein, was synthesized. In addition, a corresponding second molecule, SFLVNLGK (SEQ ID NO: 2), was synthesized, whereby the positions of the amino acids 3 and 4 were interchanged in their positions. The MS spectra of the first and second molecule are shown in FIG. 2. The most striking difference between the two MS spectra in FIG. 2 is expressed in the $y_5$-ion, which is observed as m/z 544.4 for the first peptide and as m/z 530.4 for the second molecule. Each fragment ion is specific for its precursor peptide ion, and is not observed in the MS/MS spectrum of the analogue peptide with permutated sequence. Thus, the $y_5$-ion pair is useful for relative quantification of mixtures of these two peptides.

EXAMPLE 3

To investigate the relative concentration of first/second molecule mixtures by tandem mass spectrometry, two stock solutions containing either the first molecule in form of the peptide SFVLNLGK (SEQ ID NO: 1) or the second molecule in form of the peptide SFLVNLGK (SEQ ID NO: 2) were prepared gravimetrically at equal concentrations and mixed in the following proportions: 9:1, 8:2, 7:3, 6:4, 5:5, 4:6, 3:7, 2:8, and 1:9. Collision offset plots were recorded by nano ESI QTOF tandem mass spectrometry for these mixtures as well as for the two stock solutions. An offset plot requires the sequential recording of MS/MS spectra for a series of collision offset values over a selected range. In this case, these spectra were recorded in the range of 0-60 V in steps of 1 V. From this set of data, the intensity of each fragment ion can be displayed as a function of the collision offset, as shown in FIG. 3 for the two $y_5$-ions of interest. The ion profiles in FIG. 3 show that the intensity profiles of the corresponding $y_5$-ions reflect the relative concentrations of the two peptides in the mixtures. Furthermore, the data illustrate the benefits of the truly simultaneous monitoring of the two $y_5$-ion intensities: the profile shapes for the ion pair from a given mixture are consistently identical. Possible fluctuation in the precursor ion intensity influences the profile of each $y_5$-ion in an identical manner. An expanded view of the superimposed fragment ion profile for the 1:1 mixture shows that the intensity ration does not depend on the value of the collision offset (see FIG. 4). FIG. 4 shows an overlay plot of the collision offset profile of the $y_5$-ions, a 1:1 mixture of the first peptide (m/z 544.3) and the second peptide (m/z 530.3), as recorded by nano ESI-MS/MS. Both fragment ions are formed with essentially identical abundance (equivalency limited by gravimetric preparation of stock solutions) and with identical dependence on the applied collision offset voltage. The data in FIG. 4 show, that the relative quantification of the two peptides SFVLNLGK (SEQ ID NO: 1)(first molecule peptide) and SFLVNLGK (SEQ ID NO: 2)(second molecule peptide) can be performed directly from the relative intensities of the corresponding $y_5$-ions m/z 544.3 and 530.3. In addition, the overlay plot shows that the equivalency of the result does not depend on the selected collision offset value. The most precise result will be obtained when an offset value (or the range of offset values) is selected which generates the highest fragment ion intensities.

EXAMPLE 4

To investigate the elution behaviour of three permutated peptide pairs by liquid chromatography, the positional exchange of two amino acids was performed between two adjacent positions (FIG. 5a) and between two amino acids separated by one residue (FIG. 5b) or two residues (FIG. 5c). As shown in FIG. 5, the permutation of two amino acids separated by one amino acid or two amino acids resulted in peptide pairs which could be separated completely by UPLC, whereas the permutation of two directly adjacent amino acids resulted in a peptide pair, which could not be resolved by UPLC. The effect of sequence permutations on the LC-retention time can currently not be predicted, but has to be investigated experimentally case-by-case. Nevertheless, the data in FIG. 5 show that the principle of peptide sequence permutation in the form of a minimal permutation (exchange of two homologous amino acids) is sufficient to achieve complete LC-separation and thus separate detection of the two components by LC combined with any suitable detection techniques (MS, UV, fluorescence, element-specific detector, etc.).

Experimental Details of Example 4:

LC: nanoAcquity UPLC system Waters; column: 100 µm id.×100 mm length; particles:

BEH C18; particle size: 1.7 µm; gradient LC with the following UPLC-grade solvents: water 0.1% FA and acetonitrile 0.1% FA.

MS: QTOF2, Waters micromass.

The invention claimed is:

1. A method for determining the concentration of a first molecule having a chemical structure, which contains a first peptide sequence comprising:
   (a) obtaining a sample containing the first molecule,
   (b) providing a reference sample which contains a second molecule having a certain concentration and chemical structure, which contains a second peptide sequence, wherein the chemical structure of the second molecule only differs from the structure of the first molecule in one or more permutations in the first peptide sequence,
   (c) combining the reference sample and the sample containing the first molecule,
   (d) identifying at least one fragment peak in a mass spectrum (MS) of the first molecule and the second molecule, wherein the mass difference of the fragment peaks is only caused by the permutation of the at least two different amino acids, and
   (e) determining the concentration of the first molecule relative to the certain concentration of the second molecule by comparing of the identified peaks.

2. A method according to claim 1, wherein the second molecule of known amount is added to the reference sample and the absolute concentration of the first molecule in the sample is determined in step (e) of the method of the invention.

3. A method according to claim 1, wherein the second molecule contains one permutation.

4. A method according to claim 1, wherein two non adjacent amino acids are permutated.

5. A method according to claim 1, wherein the amino acid pro line is present between the permutated amino acids.

6. A method according to claim 1, wherein two adjacent amino acids are permutated.

7. A method according to claim 1, wherein the first molecule is a pharmaceutically active compound.

8. A method according to claim 1, wherein the first molecule is obtained by linking a peptide having a peptide sequence containing the first peptide sequence to a pharmaceutically active compound.

9. A method according to claim 1, wherein the first molecule is a polypeptide.

10. A method according to claim 9, wherein the first molecule is derived from a cell, a prokaryotic cell, an eukaryotic cell, a mammalian cell, a human cell, from an organ or a human organ, from plasma or from serum.

11. A method according to claim 1, wherein the first peptide sequence has 5 to 100 amino acids.

12. A method according to claim 1, wherein at least one of the pairs of amino acids selected from the group consisting of serine and threonine; asparagine and glutamine; aspartic acid and glutamic acid; and lysine and arginine is permutated.

13. A method according to claim 1, wherein homologue amino acids are permutated.

* * * * *